United States Patent [19]

Okada et al.

[11] 4,106,100
[45] Aug. 8, 1978

[54] DIGITAL DIFFERENTIAL ANALYZER

[75] Inventors: Kunihiro Okada; Yoshiharu Itatsuda; Takeyuki Endoh; Shigeru Yabuuchi, all of Tokyo; Norio Yokozawa, Fuchu, all of Japan

[73] Assignees: Hitachi, Ltd.; Hitachi Denshi Kabushiki Kaisha, both of Japan

[21] Appl. No.: 780,457

[22] Filed: Mar. 23, 1977

[30] Foreign Application Priority Data

Mar. 24, 1976 [JP] Japan .................................. 51-31338

[51] Int. Cl.$^2$ ........................... G06J 1/02; G06F 7/38
[52] U.S. Cl. .................................................. 364/702
[58] Field of Search ................... 235/150.31, 152, 156, 235/151.11; 364/702

[56] References Cited

U.S. PATENT DOCUMENTS

| | | | |
|---|---|---|---|
| 3,419,711 | 12/1968 | Hunter et al. | 235/150.31 |
| 3,586,837 | 6/1971 | Hyatt et al. | 235/150.31 |
| 3,598,974 | 8/1971 | Lincoln | 235/150.31 |
| 3,644,723 | 2/1972 | Rosener | 235/150.31 X |
| 3,701,890 | 10/1972 | Dummermuth | 235/150.31 |

Primary Examiner—Joseph F. Ruggiero
Attorney, Agent, or Firm—Craig & Antonelli

[57] ABSTRACT

A digital differential analyzer comprises an arithmetic unit for performing an integration operation, a control unit for controlling the arithmetic unit, a plurality of temporary storage means in the arithmetic unit for temporarily storing interim results of the arithmetic operation therein to relieve the influence of propagation delay time of the arithmetic unit.

14 Claims, 8 Drawing Figures

| INPUT | | | | OPERATION TYPE | | OUTPUT | | | | | | |
|---|---|---|---|---|---|---|---|---|---|---|---|---|
| A | B | C | D | | | $G_1$ | $G_2$ | $G_3$ | $G_4$ | $G_5$ | $G_6$ | $G_7$ |
| 0 | 0 | 0 | 1 | $yd = yi - dyi$ | | 0 | 0 | 1 | 1 | 0 | 0 | 1 |
| 0 | 0 | 1 | 0 | $yd = yi$ | | 0 | 0 | 1 | 0 | 0 | 1 | 0 |
| 0 | 0 | 1 | 1 | $yd = yi - \frac{1}{2} dyi$ | | 0 | 0 | 1 | 0 | 1 | 0 | 1 |
| 0 | 1 | 0 | 0 | $yd = yi + \frac{1}{2} dyi$ | | 0 | 0 | 1 | 0 | 1 | 0 | 0 |
| 0 | 1 | 0 | 1 | $yd = yi + \frac{3}{2} dyi$ | | 0 | 0 | 0 | 0 | 1 | 0 | 1 |
| 0 | 1 | 1 | 0 | $yd = yi + \frac{5}{2} dyi$ | | 0 | 0 | 0 | 0 | 1 | 0 | 0 |
| 0 | 1 | 1 | 1 | $dz = dxi \quad yi > 0$ | | 1 | 1 | 0 | 0 | 0 | 0 | 0 |
| 1 | 0 | 0 | 0 | $dz = dxi \quad yi > 0$ $dz = dxi \quad yi < 0$ | | 0 | 1 | 0 | 0 | 0 | 0 | 0 |

DIGITAL DIFFERENTIAL ANALYZER

BACKGROUND OF THE INVENTION

The present invention relates to a digital differential analyzer for resolving a differential equation.

The digital differential analyzer (hereinafter referred to DDA) has been used as a means for resolving the differential equation and it operates based on a principle of calculating an area of segmented regions. The DDA can be classified into a serial type DDA in which a digital integrator performs operations step by step in serial and a parallel type DDA in which all of the digital integrators perform operations simultaneously. The former has advantages of low cost because an arithmetic unit including the integrator can be commonly used and of simple compensating operation and high accuracy of the result because preoperated result of the integrator can be used in the subsequent operations. Therefore, the former has been frequently used in the past. However, it has a disadvantage of low operation speed because the digital integrator performs the operations step by step. On the other hand, the latter allows a high speed operation because all of the digital integrators perform the operations simultaneously. However, since inputs (primary increment and secondary increment) to the digital integrator are always limited to those of one or more iteration times earlier, different compensating operations are required depending on the degree of delay of those inputs. As the compensating operation becomes complex, arithmetic circuits required become complex accordingly. Thus, in the parallel type DDA in which one arithmetic circuit is required for each of the digital integrators, it is difficult to attain a practical DDA unless the arithmetic circuits are constructed by a fewer number of circuit components and the operations are carried out at a high speed. Like in a conventional digital computer, the operation within the DDA can be classified into three categories, that is, a serial addition method in which data are added bit by bit, a parallel addition method in which all bits are added simultaneously and a combination thereof. The serial type DDA in which the common arithmetic unit can be used generally employs the parallel addition method in order to attain a higher operation speed while the parallel type DDA generally employs the serial addition method in order to reduce the number of components. However, since the parallel addition method is superior in the operation speed to the serial addition method, some of the parallel type DDA employ the parallel addition method to attain the high operation speed. In the parallel addition method, matching of bit positions of an integrated result and a secondary increment is necessary in producing a sum thereof and this governs the operation time of the DDA.

The DDA's of the types described above each includes an adder for calculating the integrated value, an adder for performing the compensating operation and an adder for performing quantizing operation to generate a tertiary increment, all of those adders being connected directly in cascade. When an operation is to be carried out in the DDA of the serial addition type, for example, the operations by all of the above adders are carried out for one bit of the data representative of the integrated value and then the operations are repeated for the next bit. In the DDA of the parallel addition type, after the operations for one data have been completed, the operations for the next data are carried out.

Thus, a long operation time has been heretofore been required and this has been blocking the achievement of the high speed operation.

Furthermore, only a relatively simple compensating operation could be performed and hence the parallel type DDA which required a complex compensating operation had a problem in the operation accuracy.

SUMMARY OF THE INVENTION

It is a main object of the present invention to provide a DDA which enables a high speed of operation.

It is another object of the present invention to provide a DDA capable of performing a very high precision operation.

In order to achieve the above objects, the present invention uses temporary storage means in arithmetic units such as adders for performing various operations, in order to temporarily store the interim operation results of the arithmetic unit in the temporary storage means so that the respective arithmetic units may carry out various operations simultaneously.

BRIEF DESCRIPTION OF THE DRAWINGS

FIGS. 3 to 7 show particular embodiments of portions of the circuit of FIG. 1, in which

DETAILED DESCRIPTION OF THE PREFERRED EMBODIMENTS

Before explaining an embodiment of the present invention, a principle of the present invention is first described.

An operation time of a digital integrator generally consists of a time $T_P$ required for calculating total sum of a secondary increment, a time $T_S$ required for matching bit positions in adding the secondary increment to an integrated value, and a time $T_I$ required for calculating the integrated value to generate a tertiary increment (including a time required for a compensating operation). Although the present invention can be applied either to the parallel addition method or to the serial addition method, a more remarkable advantage is attained and a fewer number of circuit components are required when it is applied to the serial addition method. Therefore, the DDA of the serial addition type is explained hereinbelow. In the serial addition type DDA, $T_S$ equals to zero because the matching of bit positions in adding the secondary increment to the integrated value can be replaced by timing for the addition thereof. As a result, the operation time T of the digital integrator in the serial addition type DDA is given by;

$$T = T_P + T_I \qquad (1)$$

where $T_P$ changes depending on an addition method for the secondary increments, and when the secondary increments are sequentially scanned for the addition by an up/down counter as described later, $T_P$ changes depending on the number of bits of the secondary increment, and when the secondary increment bits are added by an adder, $T_P$ is determined by a propagation delay time of the adder.

In the prior art DDA where the adder for calculating the integrated value, the adder for performing the compensating operation and the adder for performing the quantizing operation to calculate the tertiary increment are connected directly in cascade and all of the operations are first carried out for one bit of the data representative of the integrated value and then the operations for the next bit are carried out, the above time $T_I$ is determined by the propagation delay time $T_d$ of those adders and the number N of the bits of the data representative of the integrated value, and it is given by;

$$T_I = NT_d \qquad (2)$$

On the other hand, in the present invention where temporary storage means such as buffer registers for temporarily storing the operation results of the preceding adders are provided between the adders, the time $T_I$ can be determined in the following way. Namely, a propagation delay time $T_{dB}$ between the respective registers is given by;

$$T_{dB} = \frac{T_d}{M+1} \qquad (3)$$

where M is the number of the buffer registers provided between the adders.

Furthermore, according to the present invention, the operations can be carried out simultaneously in the respective arithmetic units by the provision of the buffer registers. For example, while the adder for performing the compensating operation is carrying out the compensating operation for one bit, the adder for performing the integration operation can carry out the integration operation for the next bit.

Accordingly, assuming that each of the adders performs the operation for one bit for each timing cycle corresponding to the propagation delay time $T_{dB}$, M bit time cycles are required before the bit stored in the first stage buffer register is stored in the last stage buffer register. Thus, (M + N) bit time cycles are required to complete the operations for the N bits. Therefore, the time $T_I$ is given by;

$$T_I = T_{dB}(M + N) \qquad (4)$$

Accordingly, the operation time T of the integrator is given by;

$$T = T_p + T_{dB}(N+M) = T_p + (\frac{N+M}{M+1})T_d \qquad (5)$$

Accordingly, if $M >> 1$, the equation (5) is represented by;

$$T \doteq T_p + (1 + \frac{N}{M})T_d \qquad (6)$$

Thus, the time $T_I$ in the prior art DDA is given by the equation (2) while the time $T_I$ in the present invention is given by the second term in the right side of the equation (6). If $N/M \geq 1$, the operation time $T_I$ of the present invention is reduced by the factor of M to compare with the prior art apparatus.

As described above, the operation time T can be considerably reduced by inserting the buffer registers between the adders. As an example, assuming that $T_P$ = 400 ns, N = 16, M = 4 and $T_d$ = 400 ns, the time T in the present invention is equal to 2.0 μs, which means the speed up of more than three times as much as the prior art apparatus in which T = 6.8 μs.

Figure 1:
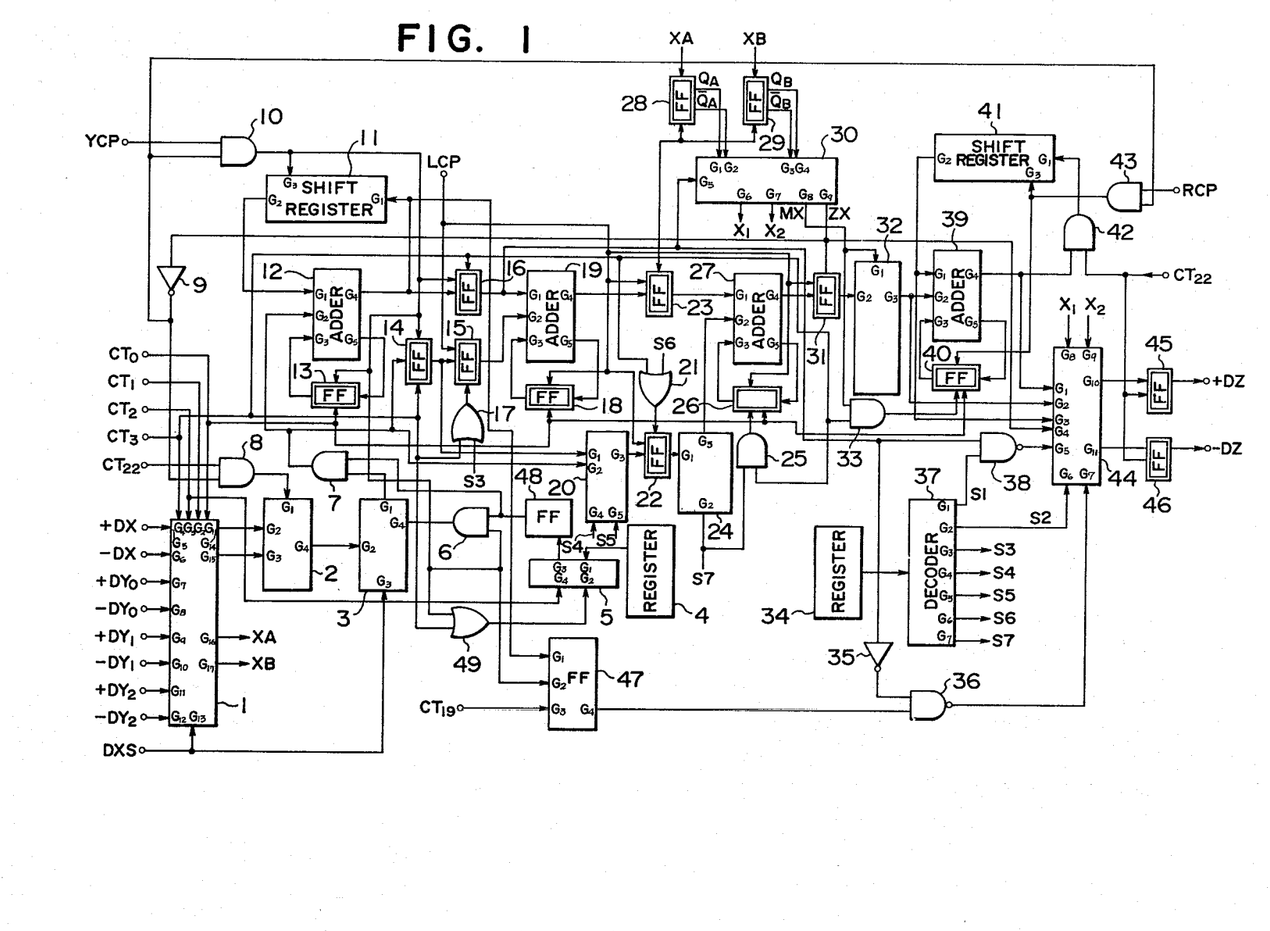
FIG. 1 shows a configuration of one embodiment of a DDA of the present invention.

FIG. 1 shows an embodiment of the DDA of the present invention constructed in accordance with the principle described above. In FIG. 1, numeral 1 denotes a selector for selecting signals $+DY_0$, $-DY_0$, $+DY_1$, $-DY_1$, $+DY_2$, $-DY_2$ corresponding to the secondary increments dy and signals $+DX$, $-DY$ corresponding to the primary increment dx, at corresponding timings, 2 denotes an up/down counter for counting up or down the secondary increments from the selector 1 to calculate a total sum of the secondary increments, 3 a shift register for adding the total sum of the secondary increments of the counter 2 to an integrated value, 28 and 29 denote flip-flops for holding the primary increment, 6, 7, 8, 10, 25, 33, 36, 38, 42, 43 denote logical AND gates, 17, 21, 49 denote logical OR gates and 9, 35 denote inverter circuits. Numerals 12, 19, 27, 39 denote one-bit adders, carry outputs of which are held in flip-flops 13, 18, 26, 40 for use as carry inputs in the addition for the next bit. Numeral 14, 15, 16, 22, 23, 31 denote buffer registers which have been additionally provided in the present invention and which comprise flip-flops in the illustrated example. Numerals 45 and 46 denote flip-flops for holding the tertiary increment dZ. Blocks circled by dual frames are D-type flip-flops. Numerals 11 and 41 denote shift registers. The shift register 11 stores an integrated value of the secondary increments dy and the shift register 41 stores the remainder of the integrated value. They are called Y register and R register, respectively. Numerals 4 and 34 denote registers. The register 4 stores a numeric value for determining addition timings of the secondary increments dy and the register 34 stores a numeric value for determining a type of operation. Although the contents of the registers 4, 11 and 34 can be externally set (e.g. from a digital computer), it is assumed for the simplification of the explanation that predetermined numeric values have been set in those registers prior to the operation. Numeral 5 denotes a counter in which the content of the register 4 is loaded. When the content reaches zero, the counter 5 produces a borrow which, in turn, sets a flip-flop 48. Numeral 37 denotes a decoder circuit for producing a signal to determine a type of operation, 44 denotes a tertiary increment decision circuit for determining the presence or absence of the tertiary increment dZ, 24 and 32 denote exclusive OR circuits for calculating 2's complements and 30 denotes a primary increment discrimination circuit for detecting positive, negative or zero value of the primary increment dx. Numeral 20 denotes a selector circuit and 47 denotes a J-K flip-flop which holds the porality of the Y register 11.

Figure 2:
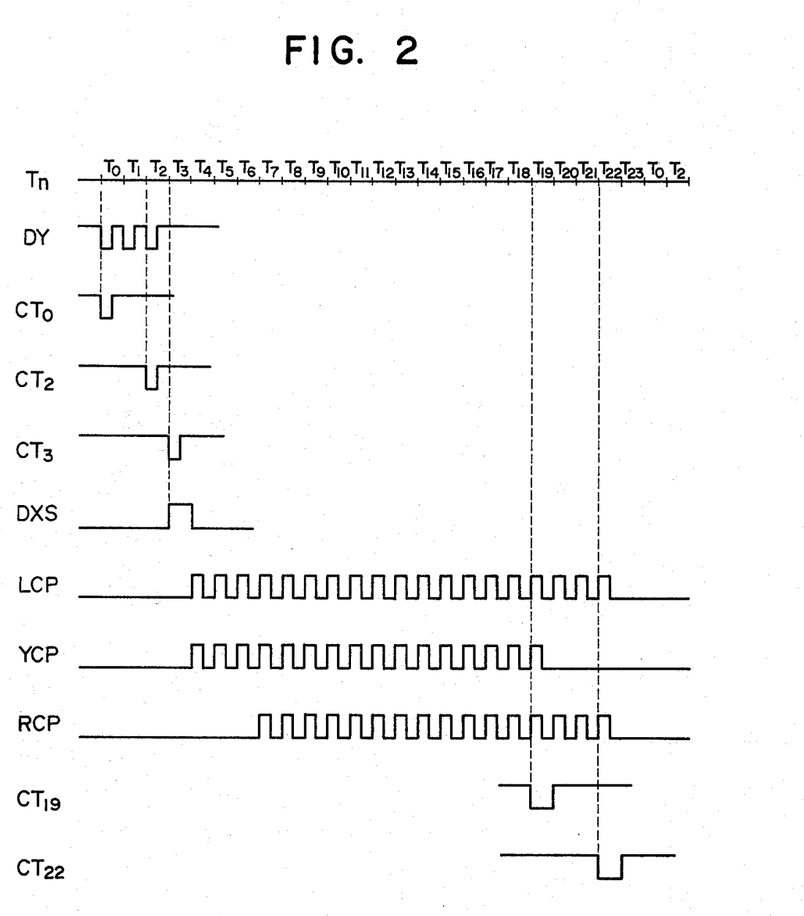
FIG. 2 is a timing chart showing operation timing of the circuit of FIG. 1.

Before explaining the operation of the circuit of FIG. 1, the timing signals applied to various points in FIG. 1 are explained in conjunction with FIG. 2. In the following example, it is assumed that the number of bits of each of the Y register 11 and the R register 41 for storing the integrated value and the remainder of the integrated value is 16, the number of inputs to which the secondary increments are applied is three and the number of input to which the primary increment is applied is one, although other numbers of bits of the registers and the inputs may be used. In FIG. 2, Tn (where n is an integer) represents timings to control the operations of the registers, flip-flops and counters in FIG. 1, and DY represents select signals for the secondary increments corresponding to clock signals $CT_0$ to $CT_2$ generated at the timings $T_0$ to $T_2$, which select signals are applied to the selector 1 to select signals $\pm DY_0$ corresponding to the secondary increment $dY_0$ at the timing $T_0$, signals $\pm DY_1$ corresponding to the secondary increment $dy_1$ at the timing $T_1$ and signals $\pm DY_2$ corresponding to the secondary increment $dy_2$ at the timing $T_2$. The clock pulse $CT_0$ generated at the timing $T_0$ functions to clear the flip-flops 13, 18, 26 and 40, and the clock pulse $CT_2$ generated at the timing $T_2$ functions to read in the content of the register 4 to the counter 5. The clock pulse $CT_3$ generated at the timing $T_3$ is applied to the selector 1 to select signals $\pm DX$ corresponding to the primary increment $dx$. The clock pulse $CT_3$ also clears the buffer registers 14, 15, 16, 22 and 23 and sets carry inputs to the flip-flops 26 and 40 in the subtraction operation. DXS represents a pulse generated during the timing $T_3$ and it sends the selected primary increment to the flip-flops 28 and 29 as the signals XA and XB and loads the total sum of the secondary increments added during the timings $T_0$ to $T_2$ into the shift register 3. LCP represents clock pulses for setting data to the buffer registers 15, 18, 22, 23, 26 and 31 and comprises 19 pulses generated at the timings $T_4$ to $T_{22}$, respectively. YCP represents shift pulses for the Y register 11 and also clock pulses for the counter 5 for determining the addition timing of the total sum $\Sigma$ $dy$ of the secondary increments and for the shift register 3 for shifting the total sum $\Sigma$ $dy$. The pulses YCP are also set pulses for the buffer registers 13, 14, 16 and 47 and comprise 16 pulses generated at the timings $T_4$ to $T_{19}$. RCP represents shift pulses for the R register 41 and also set pulses for the flip-flop 40 and comprises 16 pulses generated at the timings $T_7$ to $T_{22}$. $CT_{19}$ represents a pulse generated during the timing $T_{19}$ and it is used as $\bar{J}$ and K inputs of the J-K flip-flop 47. $CT_{22}$ represents a pulse generated during the timing $T_{22}$ and it blocks an input from the adder 39 to the R register 41, causes a sign bit of the register 41 to be positive (i.e., "0") and sets the output of the tertiary increment decision circuit 44 to the flip-flops 45 and 46.

Although the sections for generating those control signals are not shown in FIG. 1, the operation of FIG. 1 is now explained assuming that the above control signals are applied to the appropriate points in FIG. 1. The embodiment shown in FIG. 1 is designed such that it can select any of the following six values as a compensation term of the integration operation. Namely, when the compensating operation of $\pm(K/2) \Sigma$ $dyi$ is to be carried out for the integrated value $yd$, K can be selected to any of six values $-2, -1, 0, +1, +2$ and $+3$. Furthermore, it is designed such that a servo operation and a compare operation in addition to the integration operation can be carried out. The servo operation is defined as an operation for generating the tertiary increment as shown in equation (7) depending on whether the content of the Y register 11 is positive, negative or zero, and the compare operation is defined as an operation for generating the tertiary increment as shown in equation (8) depending on whether the content of the Y register 11 is positive, negative or zero.

$$\left.\begin{array}{ll} yd > 0 & dZ = dx \\ yd = 0 & dZ = 0 \\ yd < 0 & dZ = -dx \end{array}\right\} \quad (7)$$

$$\left.\begin{array}{ll} yd > 0 & dZ = +dx \\ yd \leq 0 & dZ = 0 \end{array}\right\} \quad (8)$$

where $yd = yi - 1 + \Sigma$ $dyi$ $yi - 1$: operation result of preceding iteration $\Sigma$ $dyi$: current total sum of the secondary increments In FIG. 1, the secondary increment signals $+DY_0$ and $-DY_0$ for the first bit are selected in the selector 1 by the select signal (clock pulse) $CT_0$, and the signals $+DY_1$ and $-DY_1$ for the next bit are selected by the select signal $CT_1$ and the signals $+DY_2$ and $-DY_2$ for further bit are selected by $CT_2$. The primary increment signals $+DX$ and $-DX$ are selected by the clock signals $CT_3$.

Figure 3:
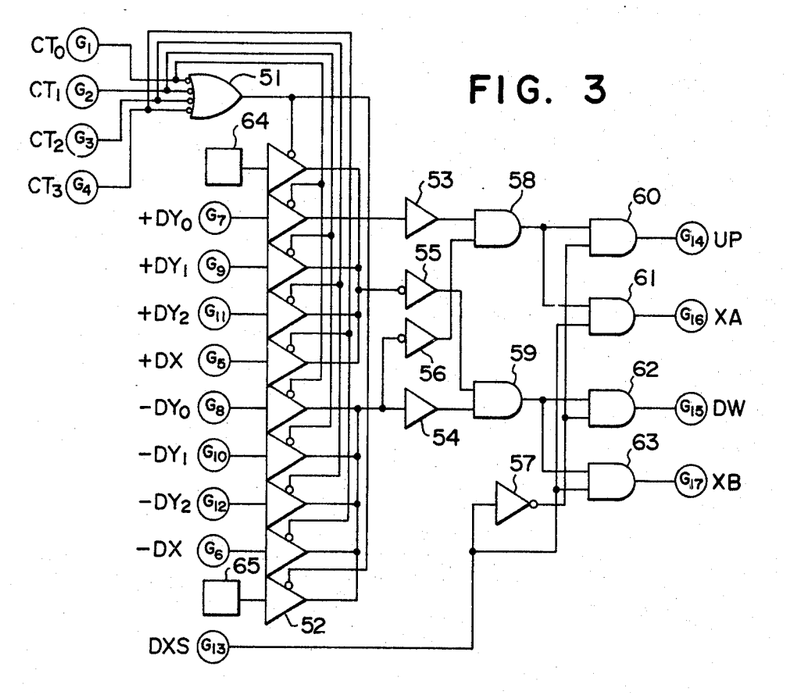
FIG. 3 shows a selector circuit.

FIG. 3 shows a particular embodiment of the selector 1 in which numeral 51 denotes an OR gate, 52 to 54 denote gates, 55 to 57 denote inverters, 58 to 63 denote AND gates, and 64 and 65 denote circuits for producing signal "1". Other reference numerals correspond to like numerals in FIG. 1.

Assuming that when the secondary increment signals $+DY$ and $-DY$ are ("1", "0"), ("0", "1") or ("0", "0") the secondary increment $dy$ is $+1, -1$ or 0 respectively, when $+DY_0 =$ "1" and $-DY_0 =$ "0" the gate 52 corresponding to the terminals $G_7$ and $G_8$ are opened by the clock pulse $CT_o$ so that signals "1" and "0" appear at the terminals $G_{14}$ and $G_{15}$ which signals are applied to the up/down counter 2 in FIG. 1 as count-up and count-down signals UP and DW. Similarly, for the primary increment, the gates 52 corresponding to the terminals $G_5$ and $G_6$ are opened by the clock pulse $CT_3$ so that the signal DXS opens the AND gates 61 and 63 to allow signals to be transmitted to the terminals $G_{16}$ and $G_{17}$. At this time, the primary increment signals XA and XB are produced at the terminals $G_{16}$ and $G_{17}$, which primary increment is set to the flip-flops 28 and 29 in FIG. 1 by the clock pulse $CT_3$. The secondary increments $dy_0$, $dy_1$ and $dy_2$ are added in the counter 2 to calculate the total sum of the secondary increments. The total sum $\Sigma$ $dy$ of the secondary increments calculated in the counter 2 is set to the shift register 3 by the pulse DXS. The shift register 3 is a four-bit shift register including three data bit positions and one sign bit position and a sign bit (not shown) is repetitively applied in order to hold the sign bit of the total sum $\Sigma$ $dy$. The shift register 3 includes three data bit positions so that, when the primary increment $dx$ is zero, the sum of the secondary increments therebetween is calculated.

Figure 4:
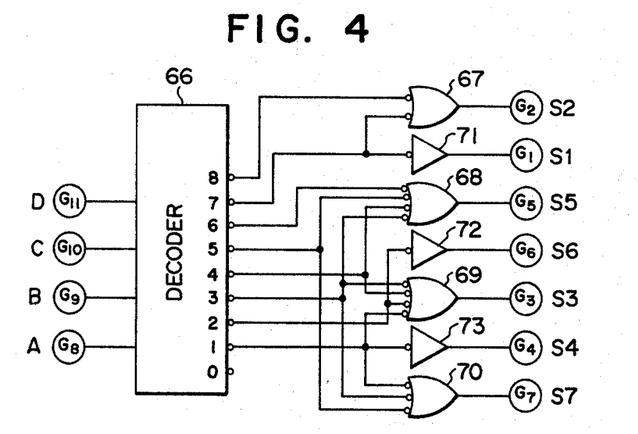
FIG. 4 shows a decoder circuit.

The total sum $\Sigma$ $dy$ of the secondary increments which has been set in the shift register 3 is added to the content of the Y register to calculate an integration value. A predetermined weighting relationship has been established between the secondary increments and the previous integration value so that the addition thereof is carried out in accordance with that relationship. The digit L is set in the register 4 of FIG. 1 with the least significant bit position of the total sum $\Sigma$ $dy$ being matched to the Lth bit position from the least significant bit position of the Y register 11, and the content of the register 4 is set to the counter 5 at the clock pulse $CT_2$. The counter 5 is counted down by the clock pulse $CT_3$ and the succeeding clock pulse YCP for shifting the Y register 11, and when the content of the counter 5 reaches zero the counter 5 produces a borrow at the terminal $G_4$ to set the flip-flop 48. The output of the flip-flop 48 causes the gates 6 and 7 to open so that the clock pulse YCP is applied to the shift register 3 and the total sum Σ dy is applied to the terminal G 2 of the adder 12 bit by bit from the least significant bit to the most significant bit through the gate 7. A bit at the timing Ti of the integrated value calculated in the adder 12 is set to the Y register 11 and at the same time set to the buffer register 16 at the same timing, and a bit of Σ dy at the timing Ti is set to the buffer register 14. Accordingly, the buffer registers 14 and 16 hold data bits of the same timing. More particularly, the data read out of the shift register 3 is set to the buffer register 16 through the propagation times in the gate 7 and the adder 12. After the integration operation for the next bit has been carried out at the timing $T_{i+1}$, the data of the buffer register 14 which has been set at the timing Ti is set in the buffer register 15 and the data bit at the timing Ti+1 is set in the buffer register 16. Accordingly, the adder 19 adds the double of the secondary increments Σ dy to the integrated value in the Y register 11. The buffer registers 22 and 23 are also set at the same timing as the buffer register 16 is set. The data set in the buffer register 22 is the data applied to the terminal G1 or G2 of the selector 20, which data is a data bit calculated one timing prior to the data bit of the secondary increments Σ dy added to the integrated value and fed from the buffer register 14 or a data bit calculated at the same timing and fed from the shift register 3. The output of the buffer register 22 is applied to the adder 27 through the exclusive OR circuit 24 which generates 2's complement so that the addition or subtraction with the data of the buffer register 23 is carried out in the adder 27. The timing relation of the data set in the buffer registers 23 and 22 is such that if the terminal G1 of the selector 20 is selected at the timing when the least significant bit of the total sum Σ dy of the secondary increments is set in the buffer register 23, the least significant bit is set in the buffer register 22, and if the terminal G2 is selected the next less significant bit is set in the buffer register 22. As a result, one half of or one time as much as the secondary increment is added to or subtracted from the integrated value as a compensation term. The compensation term may be used in the following way. As shown in the left column of FIG. 8, the data set in the register 34 is represented by inputs A, B, C and D which determine the types of operation shown in the middle column of FIG. 8. Resulting outputs at the output terminals G1 to G7 of the decoder circuit 37 are shown in the right column in FIG. 8. FIG. 4 shows an example of a detail of the decoder circuit 37, in which numeral 66 denotes a decoder, 67 to 70 denote logical OR gates and numerals 71 to 73 denote inverters. An example where A = B = D = "0" and C = "1", that is, the terminals G8, G9 and G11 are "0" and G10 is "1", is now explained. In this case, only the signals at the output terminals G3 and G5 of the decoder circuit 37 are "1". Accordingly, signals are passed to the clear terminal of the buffer register 15 through the OR gate 17 and to the terminal G5 of the selector 20 so that the terminal G2 of the adder 19 assumes "0" and the signal at the terminal G2 of the selector 20 is applied to the date input terminal of the buffer register 22. Since the signal at the input terminal G2 of the exclusive OR circuit 24 is "0" at this time, the output of the buffer register 22 is applied to the terminal G2 of the adder 27 without modification so that the compensation term of ½ Σ dyi is added to the integrated value. The output of the adder 27 is set in the buffer register 31 and it is applied at the succeeding timing to the input terminal G2 of the adder 29 through the exclusive OR circuit 32 for carrying out quantizing operation with the contents of the R register 41.

Figure 8:
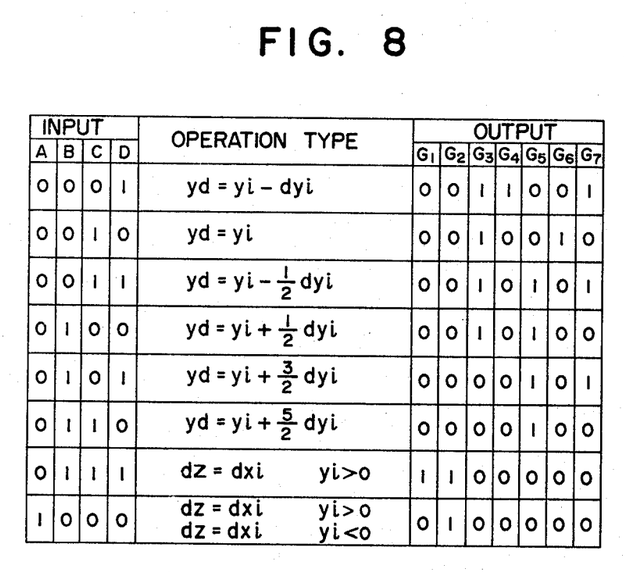
FIG. 8 shows a chart illustrating a relation between input/output of the decoder circuit of FIG. 4 and an operation type.

The compensating operation determined by the particular combination of the inputs A, B, C and D shown in FIG. 8 is carried out in the adders 19 and 27 in FIG. 1 resulting in the compensating operation for adding $-\Sigma dyi$, $-\frac{1}{2}\Sigma dyi$, 0, $+\frac{1}{2}\Sigma dyi$, $+(3/2) \Sigma dyi$ or $+(5/2) \Sigma dyi$ to the integrated value.

On the other hand, the primary increments set in the flip-flops 28 and 29 are applied to the primary increment decision circuit 30 which produces various signals.

Figure 5:
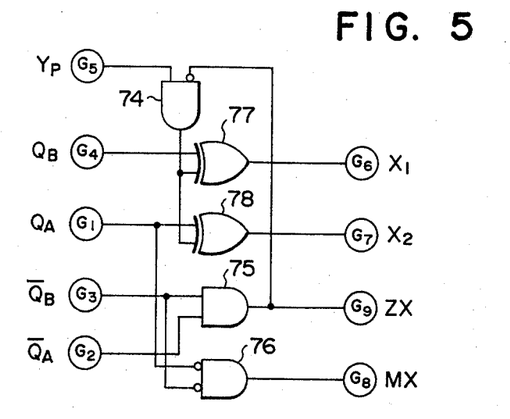
FIG. 5 shows a primary increment discrimination circuit.

FIG. 5 shows an embodiment of a particular construction of the primary increment decision circuit 30, in which numerals 74 to 76 denote AND gates, and 77 and 78 denote logical OR gates. The outputs $Q_A$ and $\overline{Q}_A$ of the flip-flop 28 are applied to the input terminals G1 and G2, the outputs $\overline{Q}_B$ and $Q_B$ of the flip-flop 29 are applied to the input terminals G3 and G4, and the integrated value in the buffer register 16 is applied to the input terminal G5. When the primary increment is zero, the output terminal G9 produces a "1" output, and when the primary increment is negative the output terminal G8 produces a "1" output. When the primary increment is positive or negative, a "1" output appears at the output terminal G6 or G7.

When the output appears at the output terminal G9, that is, when the primary increment is zero, the buffer register 31 is cleared so that the quantizing operation and the integration operation are not carried out and the application of the clock pulse is prevented by the inverter 9 and the AND gates 10 and 43 while allowing the picking up of the secondary increments to store the total sum of the secondary imcrements. When the output terminal G9 is zero, the counter 2 is cleared through the AND gate 8 by the clock pulse $CT_{22}$. When the output appears at the output terminal G8, the integrated value of the buffer register 31 is complemented by the exclusive OR circuit 32 and the flip-flop 40 is set to "1" to cause the subtraction to be carried out in the adder 39. In this manner, the operations are carried out bit by bit from the last significant bit, and when the most significant bit (sign bit) of the R register 41 is operated, that is, when the tertiary increment is generated, the AND gate 42 is closed by the clock pulse $CT_{22}$ to render the most significant bit (sign bit) of the R register 41 to be zero. This means that when the remainder of the integrated value in the R register 41 is negative, the tertiary increment −dZ is produced as will be described later and the content of the R register 41 is changed to positive value.

The presence and absence of the tertiary increment is determined by the tertiary increment decision circuit 44 based on the following equations:

$$\left. \begin{array}{l} \text{If } R_{i-1} + (Y_i \pm \frac{K}{2} \Sigma dyi)dx_i < 0; \ -dZ \\ \text{If } R_{i-1} + (Y_i \pm \frac{K}{2} \Sigma dyi)dx_i \geq 0; \ 0 \\ \text{If } R_{i-1} + (Y_i \pm \frac{K}{2} \Sigma dyi)dx_i \text{ is positive overflow;} \\ \qquad + dZ \end{array} \right\} \quad (10)$$

Figure 6:
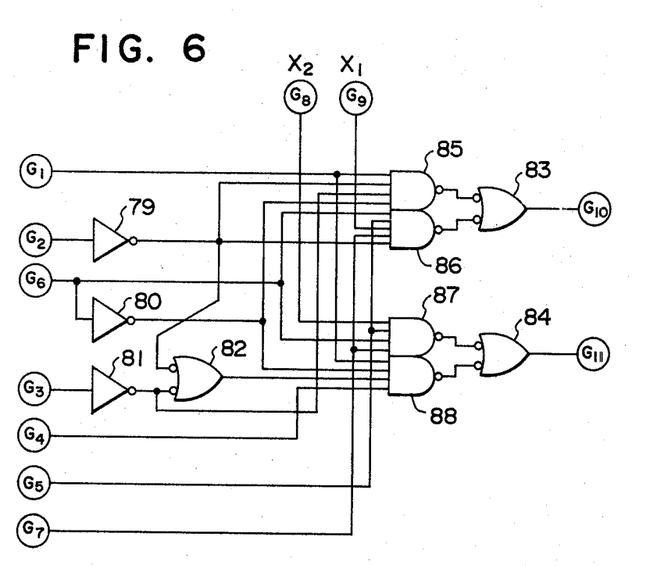
FIG. 6 shows a tertiary increment decision circuit and FIG. 7 shows a J-K flip-flop.

FIG. 6 shows an example of a particular construction of the tertiary increment decision circuit 44, in which numerals 71 to 81 denote inverters, 82 to 84 denote OR gates and 85 to 88 denote AND gates.

For example, if the sign of the integrated value which is the output from the exclusive OR circuit 32 is positive and the sign of the remainder of the integrated value in the R register 41 is positive, and if the sign of the sum thereof is negative, the tertiary increment +dZ is produced from the output terminal G10 as an overflow. If the sign of the integrated value is negative and the sign of the sum is negative, the tertiary increment −dZ is produced at the output terminal G11.

Figure 7:
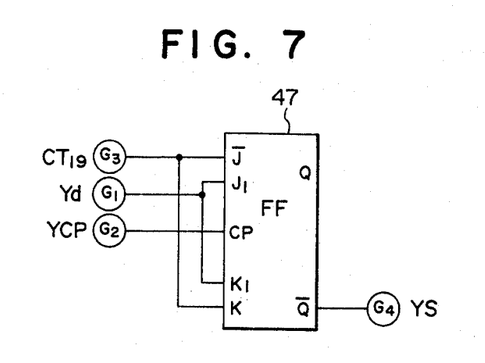

In addition to the integration operation described above, the servo operation and the compare operation can be carried out by determining the contents of the Y register 11 as described above. The method of operations is now explained below. A flip-flop 47 shown in FIG. 7 is a J-K flip-flop having a terminal G1 to which the integrated value Yd in the Y register 11 is applied and a terminal G2 to which the clock pulse YCP is applied. If the signal at the terminal G1 assumes "1" (i.e., if the integrated value is not zero) at any time during the timings $T_4$ through $T_{18}$, Q = "1" is held. If the signal at the terminal G1 is "0" at the next clock pulse $CT_{19}$, Q = "1" is maintained but if the signal at the terminal G1 is "1" (i.e., if the integrated value is negative), Q = "0" ($\overline{Q}$ = "1") is produced. Accordingly, if the output terminal G4 assumes "1", it indicates that the integrated value is negative or zero, and if the output terminal G4 assumes "0", it indicates that the integrated value is positive. On the other hand, since the buffer register 16 holds the most significant bit (sign bit) of the Y register 11 at and after the timing $T_{19}$, the results from the gates 35 and 36 prevent the signals $X_1$ and $X_2$ in FIG. 6 (i.e., the tertiary increment) from appearing because the integrated value is zero when the output of the gate 36 is "0". In the compare operation, the signals $X_1$ and $X_2$ are prevented from appearing at the outputs by the output S1 of the decoder circuit 37 and the output of the buffer register 16. Accordingly, either +dx or −dx appears at the output of the decision circuit 44 only when the content of the Y register 11 is positive in the compare operation, and when the content of the Y register 11 is not zero in the servo operation. The output of the decision circuit 44 is set in the flip-flops 45 and 46 at the clock pulse $CT_{22}$ to produce the tertiary increment signals +DZ and −DZ.

As seen from the above embodiments, according to the present invention, by providing the buffer registers 14, 15, 16, 20, 23 and 31 for holding the inputs and sums, different bits of the data can be operated simultaneously in the adders resulting in a high speed of operation.

Furthermore, data set in the buffer registers at different timings can be held, various compensating operations can be carried out allowing a high precision operation. In the prior art compensating operation, only the compensation of $\pm\frac{1}{2}\Sigma dy$ could be carried out.

While the illustrated embodiments have been shown for the serial addition type DDA, it should be understood that the present invention can be applied to a parallel addition type DDA or a combination of the serial and parallel types. In this case, however, a buffer register is required for each bit of the data. Accordingly, a fewer number of circuit components are required when the present invention is embodied in the serial addition type DDA.

It should also be understood that the present invention is applicable to both serial type and parallel type DDA's.

We claim:

1. A digital differential analyzer comprising:
input means for applying a predetermined data;
first arithmetic operation means responsive to the input data from said input means to carry out an integration operation;
second arithmetic operation means for carrying out a compensating operation for the operation result of said first arithmetic operation means;
third arithmetic operation means for carrying out a quantizing operation for the operation result of said second arithmetic operation means;
first memory means connected between said first and second arithmetic operation means for temporarily storing the operation result of said first arithmetic operation means;
second memory means connected between said second and third arithmetic operation means for temporarily storing the operation result of said second arithmetic operation means; and
control means for controlling the operations of said first through third arithmetic operation means and said first and second memory means.

2. A digital differential analyzer according to claim 1 wherein said first through third arithmetic operation means each includes an adder.

3. A digital differential analyzer according to claim 1 wherein said first and second memory means each includes a buffer register.

4. A digital differential analyzer according to claim 1 wherein said second arithmetic operation means comprises fourth and fifth arithmetic operation means for carrying out compensating operation for different values, and said second memory means comprises means for holding operation results of said fourth and fifth arithmetic operation means.

5. A digital differential analyzer comprising:
input means for applying at least one primary increment and at least one secondary increment;
first arithmetic operation means for performing an integration operation for the secondary increment from said input means;
second arithmetic operation means for performing a compensating operation for the operation result of said first arithmetic operation means by a compensation value having a predetermined relation to the secondary increment;
third arithmetic operation means responsive to the primary increment for quantizing the operation result of said second arithmetic operation means to produce a tertiary increment;
first memory means connected between said first and second arithmetic operation means for temporarily storing the operation result of said first arithmetic operation means;
second memory means connected between said second and third arithmetic operation means for temporarily storing the operation result of said second arithmetic operation means; and
control means for controlling the operations of said first through third arithmetic operation means and said first and second memory means.

6. A digital differential analyzer according to claim 5 wherein said second arithmetic operation means comprises fourth arithmetic operation means for adding or subtracting one half of the secondary increment to or from the operation result of said first arithmetic operation means, and fifth arithmetic operation means for adding or subtracting the secondary increment or double thereof, and said second memory means comprises third and fourth memory means for temporarily storing the operation results of said fourth and fifth arithmetic operation means.

7. A digital differential analyzer according to claim 5 wherein said input means comprises a selector for selectively applying the primary increment and a plurality of secondary increments and a counter for calculating a total sum of the secondary increments from said input means.

8. A digital differential analyzer according to claim 6 wherein said fourth arithmetic operation means comprises fifth memory means for temporarily storing the secondary increment from said input means, sixth memory means for temporarily storing the content of said fifth memory means, and means for adding or subtracting the content of said sixth memory means to and from the content of said first memory means.

9. A digital differential analyzer according to claim 8 wherein said fifth arithmetic operation means comprises seventh memory means for selectively storing the contents of said fifth and sixth memory means, and further comprising means for adding or subtracting the content of said seventh memory means to or from the content of said third memory means.

10. A digital differential analyzer according to claim 5 further comprising means responsive to the primary increment from said input means and the operation result of said first arithmetic operation means for performing a servo operation.

11. A digital differential analyzer according to claim 5 further comprising means responsive to the primary increment from said input means and the operation result of said first arithmetic operation means for performing a compare operation.

12. A digital differential analyzer comprising:
input means for successively applying input data;
first arithmetic operation means for performing an arithmetic operation in response to the input data from said input means;
memory means connected to said first arithmetic operation means for temporarily storing the result of the arithmetic operation by said first arithmetic operation means;
second arithmetic operation means connected to said memory means for performing an arithmetic operation in response to the contents of said memory means; and
control means connected to said first and second arithmetic operation means for controlling said first and second arithmetic operation means so that, during a period when said second arithmetic operation means performs an arithmetic operation related to preceding input data, said first arithmetic operation means performs an arithmetic operation related to subsequent input data.

13. A digital differential analyzer according to claim 12, further including additional memory means for temporarily storing the result of the arithmetic operation by said second arithmetic operation means.

14. A digital differential analyzer according to claim 12, wherein each of said first and second arithmetic operation means includes an adder.

* * * * *